United States Patent [19]

Darden et al.

[11] 4,400,565

[45] Aug. 23, 1983

[54] CO-CATALYST FOR USE WITH BORON TRIFLUORIDE IN OLEFIN OLIGOMERIZATION

[75] Inventors: Jerome W. Darden; Edward T. Marquis; Lewis W. Watts, Jr., all of Austin, Tex.

[73] Assignee: Texaco Inc., White Plains, N.Y.

[21] Appl. No.: 372,494

[22] Filed: Apr. 28, 1982

[51] Int. Cl.³ .......................... C07C 1/16; C07C 2/74; C07C 2/02

[52] U.S. Cl. ......................................... 585/10; 585/12; 585/18; 585/255; 585/510; 585/525; 585/526

[58] Field of Search ..................... 585/10, 12, 18, 255, 585/510, 522, 525, 526, 532, 643, 648, 660, 664

[56] References Cited

U.S. PATENT DOCUMENTS 3,152,998 10/1964 Moss .................................. 252/470
4,045,508 8/1977 Cupples et al. ...................... 585/511
4,065,512 12/1977 Cares ................................... 585/508
4,218,330 8/1980 Shubkin .............................. 585/255
4,300,006 11/1981 Nelson ................................ 585/255

*Primary Examiner*—Curtis R. Davis
*Attorney, Agent, or Firm*—Jack H. Park; Kenneth R. Priem; David L. Mossman

[57] ABSTRACT

A method for oligomerizing olefins in the presence of boron trifluoride and a co-catalyst comprising a heterogeneous cationic ion exchange resin catalyst is described. While the resin catalyst cannot oligomerize olefins by itself at temperatures around 75°–85° C., when used together with boron trifluoride an oligomer mixture may be created which has improved properties over oligomers made over only boron trifluoride. If a resin catalyst is used, a protonic promoter is not required.

42 Claims, No Drawings

CO-CATALYST FOR USE WITH BORON TRIFLUORIDE IN OLEFIN OLIGOMERIZATION

CROSS-REFERENCE TO RELATED APPLICATION

This application is related to co-pending patent application Ser. No. 372,491, filed of even date, which is related to the manufacture of synthetic lubricant additives over boron trifluoride in the presence of 1-butanol from mixtures of alpha and internal olefins.

BACKGROUND OF THE INVENTION

1. Field of the Invention

The invention relates to methods of oligomerizing olefins and more particularly relates to methods of oligomerizing a mixture of internal and alpha olefins over a dual catalyst system of boron trifluoride and a cationic ion exchange resin.

2. Description of Related Methods

Many researchers have believed that the oligomers from internal olefins are unsuitable for use in synthetic lubricants. Nearly all patents issued on olefin oligomerization have involved alpha olefins only. For example, see U.S. Pat. No. 3,410,925 to Eby, et al. in which alpha olefins are mixed with alkylatable aromatic hydrocarbons over a Friedel-Crafts catalyst to form an alkylation sludge which is then mixed with olefins having 3 to 18 carbon atoms which are also passed over the catalyst to produce olefin dimers. U.S. Pat. No. 3,652,706 to Saines, et al. describes the polymerization of alpha olefins having 2 to 20 carbon atoms over a Friedel-Crafts metal halide catalyst plus a hydrogen form of mordenite to produce compounds having a molecular weight between 700 and 2,500. Production of a gasoline fuel composition is described in U.S. Pat. No. 3,749,560 to Perilstein which occurs by reacting a mixture of mono olefins over a Friedel-Crafts catalyst heated to a temperature around 145° C. to produce oligomers having molecular weights between 350 to 1,500. Also, U.S. Pat. No. 3,149,178 to Hamilton, et al. reveals an improved method for making polymerized olefin synthetic lubricants via a particular distillation technique of oligomers made from alpha mono olefins using a Friedel-Crafts catalyst. Alpha olefins having six to twelve carbon atoms may be dimerized in the presence of a Friedel-Crafts catalyst according to the method described in U.S. Pat. No. 4,172,855 to Shubkin, et al.

It is also known that the term "Friedel-Crafts catalysts" includes boron trifluoride among other metal halide-type Lewis catalysts, see *Kirk-Othmer Encyclopedia of Chemical Technology*, Third Edition, Vol. 11, pg 292. Boron trifluoride has also been known to polymerize olefins, as seen in F. Albert Cotton, et al., *Advanced Inorganic Chemistry: A Comprehensive Text*, Interscience Publishers, 1962, p. 191.

A number of patents have also used $BF_3$ to oligomerize olefins. It is generally accepted that boron trifluoride will not catalyze olefin oligomerization without a promoter. Close study will reveal that alpha olefins are considered the only useful form of olefins for oligomers suitable for synthetic lubricants. For example, British Pat. No. 1,323,353 describes the use of wax cracked alpha olefins as precursors for synlube fluids. U.S. Pat. No. 2,780,664 to Serniuk describes the reaction of conjugated dienes with mono olefins over $BF_3$ promoted by an ether mixed with a halo alkane diluent at a temperature from −30 to 100° C. to produce oligomers suitable for drying oils. Alpha olefins having from 5 to 20 carbon atoms are oligomerized using $BF_3$ plus an alcohol or water promoter as described in U.S. Pat. No. 3,382,291 to Brennan. In this patent, $BF_3$ and a mixture of $BF_3$ plus the promoter complex are introduced in two separate streams. Another U.S. patent by Brennan U.S. Pat. No. 3,742,082, concerns the dimerization of alpha olefins via $BF_3$ which is promoted with phosphoric acid or water at a temperature from 100° to 150° C. U.S. Pat. No. 3,763,244 to Shubkin, which describes the oligomerization of n-alpha olefins having 6 to 16 carbon atoms over $BF_3$ promoted with water, at a temperature between 10° and 60° C. where it is preferred that $BF_3$ is added continuously.

Yet another U.S. patent to Brennan, U.S. Pat. No. 3,769,363 describes the oligomerization of olefins having 6 to 12 carbon atoms using $BF_3$ with a carboxylic acid promoter having at least 3 carbon atoms at a temperature between 0° and 20° C. to produce olefins heavy in trimer form. U.S. Pat. No. 3,780,128 also to Shubkin relates to the oligomerization of alpha olefins having 6 to 16 carbon atoms in which $BF_3$ is employed in a molar excess of alcohol. U.S. Pat. No. 3,876,720 to Heilman, et al. describes a two-step procedure by which alpha olefins having 8 to 12 carbon atoms are converted to vinylidene olefins which are then reacted over a 1:1 molar complex of $BF_3$ and alcohol to produce oligomerized vinylidene olefins. A method for oligomerizing both short and long chain alpha olefins having from 14 to 20 carbon atoms simultaneously over $BF_3$ with an alcohol or water promoter at 0° to 60° C. with a monomer recycle is described in U.S. Pat. No. 4,225,739 to Nipe, et al. There is also U.S. Pat. No. 4,263,465 to Sheng, et al. which describes a two-step process for reacting one-butene with a higher alpha olefin over $BF_3$ in the presence of a proton donor at a temperature from −30° to 50° C. to produce an oligomer having 8 to 18 carbon atoms. The intermediate oligomer is reacted with other higher alpha mono olefins over the same catalyst system from −30° to 60° C. to produce oligomers having 20 to 40 carbon atoms. For more information on $BF_3$-catalyzed oligomerization of alpha olefins, see Brennan, "Wide-Temperature Range Synthetic Hydrocarbon Fluids," Ind. Eng. Chem. Prod. Res. Dev. 1980, Vol. 19, pp. 2–6 and Shubkin, et al., "Olefin Oligomer Synthetic Lubricants: Structure and Mechanism of Formation," Ind. Eng. Chem. Prod. Res. Dev. 1980, Vol. 19, pp 15–19.

Two patents have been located which involve the reaction of internal olefins over Friedel-Crafts catalysts. U.S. Pat. No. 4,167,534 to Petrillo, et al. describes olefins which are both alpha and internal having from 10 to 15 carbon atoms which are reacted over Friedel-Crafts catalysts between 20° and 200° C. to produce oligomers. The catalysts used in the examples of this patent are only $AlCl_3$ and $NaAlCl_4$. The internal olefins are also those that are statistically distributed. U.S. Pat. No. 4,218,330 to Shubkin describes hydrogenated dimers from alpha olefins having from 12 to 18 carbon atoms, especially 1-tetradecene, made using a Friedel-Crafts catalyst, which includes therein boron trifluoride with a promoter. Shubkin's method uses predominantly alpha olefins, although the specification mentions that "fairly large amounts of internal olefins can be *tolerated* without adversely affecting the physical properties of the oligomer." (Emphasis added) This last remark from Shubkin reveals the general feeling of those working in the field that internal olefins do not produce oligomers with good properties for synthetic lubricants. For example, in U.S. Pat. No. 3,952,071 to Isa, et al., it is revealed that olefins may be oligomerized in the presence of a mixture of a polyhydric alcohol derivative and an aluminum halide. Isa, et al. mention that the olefin could be internal or alpha although alpha olefins are the only ones used in the examples therein. U.S. Pat. No. 3,947,509, also to Isa, et al., also claims that internal olefins may be used over a ketone and ester ether or alcohol promoted aluminum chloride catalyst although only alpha olefins are used in the examples.

U.S. Pat. No. 4,300,006 issued on Nov. 10, 1981. It describes a process for producing a hydrocarbon oil by contacting a mixture of alpha and at least 50 weight percent internal olefins with a boron trifluoride dimerization catalyst. However, the productivity of useful products from the process revealed in U.S. Pat. No. 4,300,006 is quite low. For example, an alkane diluent is found to be necessary in the process described therein. When the lights and heavies are distilled out, not as much useful product remains as would be hoped. Further, this method requires a much longer reaction time and a higher catalyst level than desired. It would be beneficial if a method for producing synthetic lubricants could be devised which would overcome the aforementioned disadvantages.

With specific reference to the co-catalyst of this invention, cationic ion exchange resins have been used to catalyze a number of reactions. For example, U.S. Pat. No. 4,065,512 discloses the use of perfluorosulfonic acid resin membranes to catalyze the hydration and/or polymerization of isobutene. U.S. Pat. No. 4,038,213 concerns alkylation of isoparaffins by addition of an olefin and other reactions using a supported solid perfluorinated polymer of like chemical composition to that used in U.S. Pat. No. 4,065,512. The U.S. Pat. No. 4,038,213 discloses that olefins of from C-2 to C-5 will polymerize if the isoparaffin is not used in large excess. Research Disclosure, Citation 19515, "Catalytic Uses of NAFION ® Perfluorosulfonic Acid Products", published by Industrial Opportunities, Ltd., UK (July, 1980), pp. 270–271, generally reveals that any reaction known to be catalyzed by sulfuric acid may be expected to also be catalyzed by NAFION brand ion exchange resins made by E. I. duPont de Nemours & Co., Inc.

In the field of oligomerizing olefins for synthetic lubricants, it is a continual problem to produce olefins having low viscosities at room temperature and below but which have a high viscosity index and low volatility.

SUMMARY OF THE INVENTION

The invention relates to a method for the production of olefin oligomers comprising reacting a mixture of alpha olefins and internal olefins, the mixture being such that the internal olefins comprise greater than 50 weight percent of the mixture, in the presence of boron trifluoride and a cationic ion exchange resin under oligomerization conditions.

DESCRIPTION OF THE PREFERRED EMBODIMENTS

It has been surprisingly discovered that oligomers which have an unusual blend of properties may be made by reacting alpha and internal mono olefins over a boron trifluoride catalyst and a cationic ion exchange resin, where the internal olefin component is at least 50 weight percent of the mixture. No other researchers have accomplished this objective in this way.

In the inventive method, $C_9$–$C_{24}$ internal and alpha mono olefins are charged to a vessel along with the ion exchange resin co-catalyst. The mixture is saturated with $BF_3$ and allowed to react to completion. Oligomerization may be conducted either in batch or a continuous mode. Monomer is removed for recycle after the ion exchange resin is removed by filtration. The resin can be washed and recycled. The bottoms product is hydrogenated using conventional nickel catalysts and conventional technology. The oligomerized olefins can also be hydrogenated before monomer is removed. The resulting hydrogenated oligomer is the desired synlube fluid.

The alpha olefins to be oligomerized in this invention may be obtained by a multi-step process. In the first step, ethylene is transformed into linear alpha olefins using Ziegler technology as disclosed in various patents, including U.S. Pat. Nos. 3,424,815; 3,482,000; 3,424,816; 3,444,264; 3,444,263; 3,502,741; 3,510,539; 3,478,124; and 3,441,631. These patents are incorporated herein by reference. The result of this conversion of ethylene is a mixture of alpha olefins ranging from C-4 to above C-24. The alpha olefins ranging from about C-9 to C-24 or any other range of alpha olefins desired within C-9 to C-24 are separated and oligomerized using the dual catalyst system of this invention. The alpha olefins of below about 9 and above about 24 carbon atoms are combined and subjected to an isomerization/disproportionation process described in the literature, for example: U.S. Pat. Nos. 3,647,906; 3,728,414 and 3,726,938, which are incorporated herein by reference.

The olefins resulting from this isomerization/disproportionation process are a mixture of alpha and internal olefins of various molecular weights. The olefins in the range from about 9 to 24 carbon atoms or any selected cut within that range may be oligomerized with the dual catalyst system. Optionally, those olefins may be mixed with the alpha olefins from the initial ethylene made feed and oligomerized. The olefins lying outside the range to be oligomerized are combined and subjected to the isomerization/disproportionation process again. This process can be carried on indefinitely.

Such a process provides a systematic way to control which olefin cut is selected for oligomerization, and also uses the discarded cuts for additional feed. Olefins useful in the method of this invention may also be produced by wax pyrolysis.

Generally, both kinds of olefins should have between 9 and 24 carbon atoms, inclusive. It is especially preferred that the olefins have between 13 and 15 carbon atoms inclusive. The internal olefins used herein have the double bond randomly distributed across the molecule. In this context, the term "randomly distributed" means that the double bond in the internal olefin is not predominantly in any one location. For example, an olefin mixture being comprised of a majority of alpha olefins would be outside the scope of this definition since the double bond would be located predominantly between the first and second carbon atoms of the molecules. Likewise, since the internal olefins used for oligomerization in the method of U.S. Pat. No. 4,300,006 are made by disproportionation of alpha olefins, the double bond is located predominantly at or near the center of the molecule, and such olefin feedstocks also fall outside the definition of having a "random distribution" of the double bond. A random distribution includes the distribution one may obtain upon the dehydrogenation of parafins. One would expect a small amount of alpha olefin to result from such a distribution. However, it would also be anticipated that the alpha olefin proportion would only be about 0.1 weight percent, with a maximum value being about 1.0 weight percent. The double bond would appear in all possible positions. Internal olefin mixtures are potentially more available than the pure cut alpha olefins and are potentially as cheap or cheaper than the corresponding pure cut alphas.

The olefin feedstock may be generally expressed as a mixture of compounds comprising alpha olefins having the formula $$R''CH{=}CH_2$$

where $R''$ is an alkyl radical of 7 to 22 carbon atoms and 50 weight percent or more of internal olefins having the formula $$RCH{=}CHR'$$

where R and R' are the same or different alkyl radicals of 1 to 21 carbon atoms. However, the total number of carbon atoms in any one olefin molecule should be within the range of 9 to 24, inclusive, with an especially preferred range being between 13 and 15, inclusive.

In addition, it should be noted that the method revealed in U.S. Pat. No. 4,300,006, incorporated by reference herein, requires that the dimerization feedstock be obtained from the disproportionation of alpha olefins having 8 to 10 carbon atoms. As a result, the dimerization feedstocks therein are a mixture of alpha and internal olefins where the alpha olefins have slightly more than half the carbon number of the corresponding internal olefin and the internal olefins are highly symmetrical (being formed from the disproportionation of two alpha olefins). The inventive method uses instead alpha and internal olefins having identical or close carbon numbers, and internal olefins where the double bond is randomly distributed instead of located in the center of a symmetrical mono olefin. These differences in the feedstocks would cause important differences in the properties of the resulting oligomers.

One way of expressing the fact that the alpha and internal olefins have carbon numbers in proximity (the feedstocks useful in this invention) is to say that the carbon numbers of the alpha and internal olefins are identical to or within one carbon of each other. For example, if an alpha olefin had a carbon number of 14, then the internal olefin present should have a carbon number in the range from 13 to 15, inclusive. Of course, if the olefin mixture had two alpha olefins of 13 and 14 carbons then internal olefins could have 12 to 15 carbon atoms, inclusive. As defined, the carbon numbers of the alpha olefins can likewise range around the carbon numbers of the internal olefins. It should be noted that the definition does not require that olefins of the permissible carbon range be present, it only requires that the carbon numbers of the alpha and internal olefins be in proximity. If a mixture included an alpha olefin of 8 and an internal olefin of 14 carbon atoms (such as a disproportionation product), it would fall outside the proximity definition.

As has been noted earlier, boron trifluoride is known as a catalyst for olefin oligomerization. However, when $BF_3$ is used as an oligomerization catalyst, most researchers find it necessary to employ a promoter. A number of different kinds of promoters may be used, and alcohols, carboxylic acids and water are frequently employed. A frequently preferred promotor is n-butanol. However, in accordance with the method of this invention, no promoter is required if a cationic ion exchange resin is used as a co-catalyst. Surprisingly, the oligomers produced by this method have excellent properties.

There are a number of different kinds of cationic ion exchange resins. Perfluorosulfonic acid resins are preferred because they resist degradation at high temperatures better than other catalysts. The perfluorosulfonic acid resins are co-polymers of sulfonyl fluorovinyl ether and a fluorocarbon and may have the following formula:

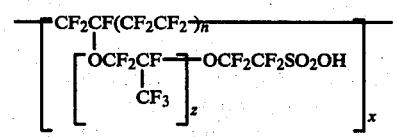

where X represents repeating units. Actually the so called XR resin (the sulfonyl fluoride form) is produced first and made into film. Then the fluoride film is hydrolyzed to the sodium sulfonate, which is finally converted to the acid form.

The formula weight corresponding to one sulfonyl acid group is called the equivalent weight. The properties of the resin depend on the equivalent weight; the higher the equivalent weight, the higher is the mechanical strength, but also the higher is the electrical resistance. Perfluorosulfonic acid resin with useful properties has an equivalent weight ranging from 1,100 to 1,500, corresponding to $z=1$, and $n=15$ to 20.

The commercial resin is available as a membrane 5 to 10 mils thick and is sometimes laminated with a polytetrafluoroethylene web to improve mechanical strength and dimensional stability. The resin is also available in pellet and powder form. The physical form of the resin is a matter of choice for one skilled in the art. All forms will provide the catalytic effect of this invention. Engineering considerations will determine the most suitable physical form.

The amount of cationic ion exchange resin that is employed is preferably between 0.1 and 10 weight percent of the total olefin charge. It is especially preferred that the amount be about 2 weight percent of the olefin charge.

A further description of the perfluorosulfonic acid resin is given in duPont "Innovation", Volume 4, No. 3, Spring, 1973 and in U.S. Pat. No. 4,038,213 and patents mentioned therein which are incorporated herein by reference.

We have discovered that the perfluorosulfonic acid resins in the acid form are very selective catalysts for the formation of lower oligomers of alpha olefins. Olefins as described above contacted with the perfluorosulfonic acid resins and boron trifluoride described above oligomerize in a highly selective manner to dimer, trimer, and vanishing amounts of tetramer. The oligomerization occurs both in the batch treatment and the continuous treatment. The batch or continuous treatment yields oligomers which usually contain high ratios of dimer to trimer and high ratios of trimer to tetramer.

The oligomerization occurs neat (no solvent needed) and at temperatures from 25° to 100° C. This temperature range is much lower than that which is required if a cationic ion exchange resin is used as the only catalyst. Depending on which olefin is used, there is a threshold temperature at which oligomerization will proceed if only the resin is present. Below the threshold temperature little or no reaction occurs. This temperature is generally in the range of 100° to 200° C., and is frequently 150° C. or higher. It is especially preferred that the reaction be conducted at a temperature around 75° to 85° C.

The reaction can proceed at autogenous pressures. However, if superatmospheric pressures are found to be advantageous, they are also acceptable. It is expected that the reaction could be advantageously run at pressures between about 10 to 2,000 psig. In a continuous process, the liquid hourly space velocity (LHSV) may vary over a wide range. One skilled in the art can adjust the LHSV to suit the particular situation. It is anticipated that one skilled in the art could adapt this method to a batch mode of operation.

The method of our invention makes valuable lower oligomers selectively using a solid fixed bed catalyst plus boron trifluoride. It is surprising that such high dimer to trimer selectivity occurs at good conversions, yet the reaction terminates before high molecular weight species are formed in appreciable quantities.

In order to form materials which have adequate oxidative stability for lubricants, the oligomerized olefins are optionally hydrogenated either partially or totally. This hydrogenation is done by procedures known to those skilled in the art as exemplified by U.S. Pat. Nos. 4,045,508; 4,013,736; 3,997,622 and 3,997,621. A particularly preferred catalyst for this hydrogenation is a nickel, copper, chromia catalyst described in U.S. Pat. No. 3,152,998 incorporated by reference herein. A cobalt-copper-chromia catalyst described therein would also be useful. The hydrogenation could be conducted in a batch or continuous manner.

Emphasis should be placed on the fact that the synthetic lubricant components of the instant invention are preferably used without further distillation after hydrogenation and monomer removal steps. In other words, the undistilled bottoms are the finished synthetic lubricant component. Typically, other oligomer mixtures must be distilled into "2 centistoke", "4 centistoke", "6 centistoke", etc. fractions before they can be useful. The viscosities refer to the viscosity of the component at 210° F. Components made by one of the preferred embodiments of this invention make excellent "4 centistoke" components without distillation beyond mere monomer removal. Thus, the method of this invention does not require a costly distillation step, which is an important advantage over methods used by others in the field. The monomer stripping step should be conducted under mild conditions. It was discovered that distillations conducted at a high temperature, 210°-290° C., would cause the oligomers to break down in some fashion and come off as volatiles. It is, therefore, important that monomer removal be accomplished at as mild conditions as possible; that is, the reboiler or pot temperature should preferably by kept at or under 180° C. when stripping out monomer. It will be shown that the method of this invention affords higher quality products than those obtained with $BF_3$ alone or a cationic ion exchange resin alone.

The following examples will illustrate the invention but are not intended to be limiting. First, the experimental methods will be described, and then the results will be tabulated.

EXAMPLE I

Oligomerization

The internal olefins used in all of these examples is a $C_{13-14}$ blend comprising 56 weight percent of $C_{13}$ internal olefin and 44 weight percent of $C_{14}$ internal olefin and produced by Shell's Higher Olefin Process (SHOP) of Shell Chemical Co.

To a 500 ml round bottomed flask fitted with magnetic stirrer, condenser, thermometer and dropping funnel was added 250 g $C_{13-14}$ internal olefin[1] and 6.4 g NAFION ® 501[2] ion exchange resin in the H+ form, (2.06% by weight of total olefin charge). The dropping funnel was filled with 60 g $C_{13-15}$ wax cracked alpha olefin from Chevron Chemical Co. The mixture was heated to 75° C. with $N_2$ purge. Boron trifluoride addition was begun at 75° C. and continued throughout the reaction. The contents of the dropping funnel were added over a 1 hour period, after which the mixture was heated to 85° and allowed to react for 2 hours. The $BF_3$ was neutralized with $Na_2CO_3$ plus water, and the solution water washed twice. The blend was filtered to remove $H_2O$ and NAFION. Liquid chromatography analysis showed 26% monomer, 59% dimer and 15% trimer.

[1] Similar olefin mixtures are obtained by the isomerization/disproportionation process disclosed heretofore.
[2] NAFION 501 is a powdered form of perfluorosulfonic acid resin. All examples use the acid form of the resin. Product of E. I. duPont de Nemours & Co.

Hydrogenation

To a stainless steel autoclave was charged 247.6 g of the above feed followed by 12.4 g of nickel, copper and chromia hydrogenation-dehydrogenation catalyst of U.S. Pat. No. 3,152,998, hereafter called nickel catalyst (5.0% by weight of olefin charge). The autoclave was pressurized with hydrogen to 1,000 psig. The mixture was heated to 210° C. and the clave repressured with hydrogen to 2,000 psig as necessary. The contents were heated and stirred at 210° C. for 4 hours and then cooled.

Monomer Removal

The hydrogenation catalyst of the above step was removed by filtration, and 218.1 g of the hydrogenated oligomers were charged to a 500 ml flask. Low boiling paraffin (monomer) was removed under 0.25-0.50 mm of vacuum to a pot temperature of 190°-200° C. Liquid chromatography analysis of the bottoms product showed 77.1% dimer, 17.9% trimer and 2.0% tetramer.

Oligomer Properties

The oligomer obtained in this example had the following properties: 210° F. viscosity at 3.75 centistokes, viscosity index of 123.2, pour point less than −50° F., 88.0% of the sample remaining at 233° C. in thermogravimetric analysis (TGA).

Viscosity at a standard temperature is given for all examples in centistokes. The viscosity index (VI) is the change in viscosity with temperature such that the higher the number, the lower is the change in viscosity with temperature. Conversely, a low VI signifies a large change in viscosity with temperature. Pour point is a measure of the temperature, in degrees Fahrenheit, at which the sample will begin to pour. Below that temperature the composition may generally be regarded as a solid. The thermogravimetric analysis (TGA) is a means to measure volatility by measuring the weight percent of sample remaining at various temperatures as the temperature is raised in a slow, uniform manner, usually 10° C./minute. Having at least 80% of the sample remaining at 233° C. is about the cut-off point for useful oligomers. A good oligomer mixture has a less than 10% distillation loss at about 700° F.

EXAMPLE II

Oligomerization

To a stainless steel autoclave was charged 1,143 g $C_{13-14}$ internal olefin mixture from Shell consisting of 56% $C_{13}$ and 44% $C_{14}$, 357 g $C_{13-15}$ wax cracked alpha olefins, and 30 g NAFION 501 ion exchange resin in the H+ form (2.0 wt.% of olefin charge). The clave was flushed with $N_2$ three or four times. The clave was heated to 75°, then pressured to 50 psig with $BF_3$. The mixture was heated and stirred at 75°–85° for four hours, and repressurized with $BF_3$ as necessary. Boron trifluoride was hydrolyzed by adding 400 ml $H_2O$ and stirring for one hour. Liquid chromatography analysis showed 39.6% monomer, 49.5% dimer and 11.0% trimer. NAFION was removed by filtration.

Hydrogenation

To a stainless steel autoclave was charged 1,265 g of feed as above, followed by 63.3 g of nickel catalyst (5.0 wt.% of olefin charge). The clave was pressured with hydrogen to 1,000 psig, then heated to 210° C. The clave was repressured with hydrogen to 2,000 psig as necessary. The oligomer was stirred at 210° C. for 4 hours, then cooled and poured.

Monomer Removal

The hydrogenation catalyst was removed by filtration. Subsequently, 1,227 g of the paraffin obtained in the above step was charged to a 2 liter flask. Low boiling paraffin was removed by distillation under 0.25–0.50 mm pressure to a pot temperature of 190°–200° C. Gel permeation chromatography analysis of the bottoms product showed 80.6% dimer and 19.4% trimer.

Oligomer Properties

The oligomer obtained in the above step had the following properties: 210° F. viscosity of 3.89 centistokes, a pour point of less than −50° F., a viscosity index of 122.3, and 90.4% of the sample remaining in TGA at 233° C.

COMPARATIVE EXAMPLES

EXAMPLE III

This example will demonstrate that the use of a cationic ion exchange resin catalyst alone without boron trifluoride at this temperature is unsatisfactory.

To a 500 ml flask fitted as in Example I was added 250 g $C_{13-14}$ internal olefin, 60 g $C_{13-15}$ wax cracked alpha olefins, and 6.8 g NAFION 501 ion exchange resin in the H+ form. The solution was heated at 85° for 4 hours. NAFION was removed by filtration. Liquid chromatography analysis showed 100% monomer after 4 hours. No reaction had occurred.

EXAMPLE IV

Example IV will demonstrate that the perfluorosulfonic acid resin of Examples I through II will catalyze the oligomerization of olefins by itself, but at an elevated temperature.

Oligomerization

To a 1000 ml round bottom flask fitted with mechanical stirrer, condenser, $N_2$ inlet and bubbler, and thermometer were added 500 grams of Shell's C-13/C-14 mixed internal olefins (53.4%, C-13, 45.0% C-14, 0.5% C-15, and 1.1% hydrocarbon) and 5.0 grams of NAFION 501 ion exchange resin catalyst in the H+ form. The reaction mixture was heated at 150° C. with stirring for 19¾ hours. The catalyst was removed by filtration. Gel permeation chromatography indicated conversion to C-26 and higher carbon oligomers was approximately 83.6% (C-13/C-14 ≅16.4%, C-26/27/28 ≅69.1%, C-39/40/41/42 ≅14.5%).

Hydrogenation

To a 1-liter stainless steel autoclave was added 300.0 grams of oligomer made in the above step and 15.0 grams of nickel catalyst in powdered form. The reaction mixture was stirred at 210° C. in the presence of 2000 psig hydrogen pressure for four hours. The catalyst was removed by filtration and the clear, nearly water-white fluid had the following properties after removal of monomer under high vacuum stripping to a pot temperature of 180° C.

Viscosity, 210° F., cst=3.93
VI=92.3
Pour point=<−50° F.

OTHER COMPARATIVE EXAMPLES

Examples V through X will illustrate oligomerization of an internal/alpha olefin blend using boron trifluoride only as the catalyst to demonstrate the superiority of the co-catalyst system of this invention by means of the resulting oligomer properties.

EXAMPLE V

To a 1 gallon stainless steel atuoclave were charged 500 grams of feed. The feed consisted of a mixture of 945 g $C_{14}$ alpha olefin made by Gulf Oil Chemicals Co., and 1145 g $C_{13}$-$C_{14}$ internal olefin. Thirty-two grams of $BF_3$ were then added with stirring. The clave was heated to 35°–40° C. To the mixture were added 1600 g of the feed along with 19 g 1-butanol slowly over a 3 hour period. The mixture was stirred at 35°–40° C. for 1.5 hours, then hydrolyzed with $H_2O$. After three $H_2O$ washes of 200 ml each, a sample was dried and submitted for liquid chromatography analysis. Liquid chromatography showed 4% monomer, 37% dimer, 41% trimer, 15% tetramer and 3% pentamer.

EXAMPLE VI

Oligomerization

To a 1 liter round bottom flask fitted with magnetic stirrer, thermometer, $BF_3$ sparge tube, and dropping funnel were added 220 g $C_{13}$-$C_{14}$ internal olefin made by Shell Chemical Co. The solution was heated to 75° C. under $N_2$ purge. The solution was saturated with $BF_3$. To the dropping funnel was added 200 g $C_{14}$ alpha olefin from Shell Chemical Co. made from ethylene polymerization, and 3.9 g 1-butanol. The contents of the dropping funnel were added over a 10 minute period, and the solution heated to 85° C. The mixture's temperature was held at 85° C. for 1 hour, cooled to room temperature, and water washed three times to hydrolyze $BF_3$. Liquid chromatography analysis showed 7% monomer, 59% dimer, 26% trimer, and 8% tetramer.

Hydrogenation

To a stainless steel autoclave was charged 353 g of the oligomer obtained in the above step followed by 17.7 g of finely ground nickel catalyst. The clave was pressured to 1,000 psig with hydrogen and heated to 210° C. The clave was repressured to 2,000 psig where the contents were held at 210° C. with stirring for four hours.

Monomer Removal

To a 500 round bottom flask equipped with magnetic stirrer and thermometer were added 310.8 g of the hydrogenated, nickel free oligomer from the above step. The pot was heated to 190°–195° C. at 0.20 mm Hg, and subsequently 87.6% of the charge was recovered as bottoms product. Liquid chromatography analysis of the bottoms product showed 57% dimer, 27% trimer, 12% tetramer and 4% pentamer.

Oligomer Properties

The oligomer obtained in this example had the following properties: 210° F. viscosity of 4.27 centistokes, viscosity index of 132, 92.2% remaining in TGA at 233° C., $-30°$ C. viscosity of 1070 centipoise, and pour point of $-35°$ F.

EXAMPLE VII

Oligomerization

To a 2 liter round bottom flask fitted as in Example 13 was added 404 g $C_{13}14$ $C_{14}$ internal olefin from Shell Chemical Co. that was 56% $C_{13}$. The solution was heated to 75° C. under $N_2$ purge, then saturated with $BF_3$. The dropping funnel was filled with 54 g $C_{14}$ alpha olefin from Shell Chemical Co. and 46 g of $C_{13}$–$C_{14}$ internal olefin (56% $C_{13}$) and 4.5 g 1-butanol. Contents of the dropping funnel were added over 10 minutes, then heated to 85° C. and held for one hour. The $BF_3$ was neutralized with $Na_2CO_3$ and the solution water washed two times. Liquid chromatography analysis showed 11% monomer, 65% dimer, 20% trimer, and 4% tetramer.

Hydrogenation

To a stainless steel autoclave was added 441.7 g of the product obtained in the above step followed by 22.1 g of nickel catalyst. The clave was pressured to 1,000 psig hydrogen and heated to 210° C. The clave was repressured to 2,000 psig, heated and stirred at 210° C. for 4 hours.

Monomer Removal

To a 1,000 ml flask fitted with thermometer and magnetic stirrer was added 398.5 g of the nickel free hydrogenated product from the above step. The blend was heated to a pot temperature of 200° C. at 0.35 mm Hg. Subsequently, 81.8% of the charge was recovered as bottoms. Liquid chromatography analysis of the product showed 67% dimer, 25% trimer, and 8% tetramer and pentamer.

Oligomer Properties

The oligomer of this example had the following properties: 210° F. viscosity of the 3.92 cs, viscosity index of 125.9, pour point of less than $-50°$ F., and 90.7% remaining in TGA at 233° C.

EXAMPLE VIII

To a 1-liter flask fitted with magnetic stirrer, thermometer, $BF_3$ sparge tube, condenser, and dropping funnel were added 225 g $C_{13}$–$C_{14}$ internal olefins from Shell Chemical Co. These internal olefins are 56 weight percent $C_{13}$ and are the same ones used in Examples IX and X. The solution was purged with $N_2$ for 30 minutes, then saturated with $BF_3$. The dropping funnel was filled with 220 g $C_{13}$–$C_{15}$ wax cracked alpha olefins from Chevron Chemical Co. having the following composition: 40% $C_{13}$, 40% $C_{14}$, and 20% $C_{15}$. These alpha olefins were also the ones used in Examples IX and X. Also added to the dropping funnel were 4 g of 1-butanol. Two hundred grams of the contents of the dropping funnel were added over a two hour period at 35°–40° C. Boron trifluoride was present in excess. After another hour, $H_2O$ was added to hydrolyze $BF_3$. The solution was washed three times. Liquid chromatography analysis of the product showed 75% monomer, 18% dimer, and 7% trimer.

EXAMPLE IX

Oligomerization

To a 1-liter flask fitted as in Example VIII were added 225 g $C_{13}$–$C_{14}$ internal olefin and 0.6 g 1-butanol. The apparatus was purged with $N_2$ for 30 minutes, then saturated with $BF_3$. The dropping funnel was filled with 110 g of $C_{13}$–$C_{14}$ internal olefin, 110 g $C_{13}$–$C_{15}$ wax cracked alpha olefins, and 3.3 g of 1-butanol. Two hundred grams of this feed were added over a two hour period at 25° C. The blend was heated to 85° and held there for 0.5 hours. The solution was cooled to room temperature and the $BF_3$ hydrolyzed with $H_2O$. Liquid chromatography analysis of the product showed 7% monomer, 56% dimer, 25% trimer, and 12% tetramer and pentamer.

Monomer Removal

To a 1 liter pot fitted with magnetic stirrer and thermometer was added 373.8 g of the product from the above step. The monomer was removed by heating to a pot temperature of 190° with pressure at 1.2 mm Hg. Subsequently, 87.3% of the charge weight was recovered as bottoms. Liquid chromatography analysis showed a trace of monomer, 58% dimer, 28% trimer, and 13% tetramer and pentamer.

Hydrogenation

To a stainless steel autoclave were charged 286.5 g of the monomer free product from the above step, along with 14.3 g of nickel-copper-chromia hydrogenation catalyst. The clave was pressurized to 1,000 psig hydrogen, and the contents heated to 210° C. The clave was repressured to 2,000 psig, and the contents stirred and reacted for four hours at 210° C.

Oligomer Properties

The monomer free, hydrogenated product of this example had the following properties: 210° F. viscosity of 4.16 centistokes, pour point of $-50°$ F., a viscosity index of 135.9, and 87.3% remaining at 233° C. in TGA.

EXAMPLE X

Oligomerization

To a 500 ml flask fitted as in Example VIII were added 200 g $C_{13}-C_{14}$ internal olefin and 45 g $C_{13}-C_{15}$ wax cracked alpha olefins. The mixture was heated to 75° under $N_2$ purge, then saturated with $BF_3$. The dropping funnel was filled with 50 g $C_{13}-C_{14}$ internal olefin and 15 g $C_{13}-C_{15}$ wax cracked alpha olefin and 2.8 g of 1-butanol. The contents of the dropping funnel were added to the pot over a one hour period. The blend was heated to 85° and allowed to react for an additional hour. Boron trifluoride was neutralized with $Na_2CO_3$ in $H_2O$, and the blend washed with water twice. Liquid chromatography analysis showed 20% monomer, 56% dimer, 16% trimer, and 8% tetramer.

Hydrogenation

To a stainless steel autoclave were charged 265.0 g of the product obtained in the above step and 13.3 g of nickel-copper-chromia hydrogenation catalyst. The clave was pressured to 1,000 psig hydrogen and heated to 210° C. The clave was repressured to 2,000 psig, and the contents stirred and heated at 210° C. for four hours.

Monomer Removal

To a 500 ml flask were charged 222.1 g of the nickel free, hydrogenated product from the above step. The pot was equipped with magnetic stirrer and thermometer. The contents of the pot were heated to 190°-195° C. pot temperature with 0.10-0.20 mm Hg. Subsequently, 65.6% of the charge was recovered as bottoms. Liquid chromatography analysis showed 73% dimer, 20% trimer, and 7% tetramer.

Oligomer Properties

The bottoms product from the step above had the following properties: 210° F. viscosity of 3.91 centistokes, viscosity index of 131.4, pour point of -50° F., 90.7% remaining in TGA at 233° C.

A brief summary of each example is presented in Tables I and II for convenient comparison.

TABLE I

| | REACTION CONDITIONS | | | | |
|---|---|---|---|---|---|
| | Feed, wt. %,[1] | | Catalyst, wt. %, | | Temp., |
| Example | Alpha | Internal | $BF_3$ | Resin | °C. |
| I | 19.4 $C_{13-15}$ | 80.6 $C_{13-14}$ | Sat.[2] | 2.0 | 75-85 |
| II | 23.8 $C_{13-15}$ | 76.2 $C_{13-14}$ | Sat. | 2.0 | 75-85 |
| III | 19.4 $C_{13-15}$ | 80.6 $C_{13-14}$ | None | 2.2 | 85 |
| IV | — | 100.0 $C_{13-14}$ | None | 1.0 | 150 |
| V[3] | 45.2 $C_{14}$ | 54.8 $C_{13-14}$ | 1.5 | None | 35-40 |
| VI | 47.6 $C_{14}$ | 52.3 $C_{13-14}$ | Sat. | None | 75-85 |
| VII | 10.7 $C_{14}$ | 89.3 $C_{13-14}$ | Sat. | None | 78-85 |
| VIII | 47.1 $C_{13-15}$ | 52.9 $C_{13-14}$ | Sat. | None | 34-40 |
| IX | 23.5 $C_{13-15}$ | 76.5 $C_{13-14}$ | Sat. | None | 85 |
| X | 19.4 $C_{13-15}$ | 80.6 $C_{13-14}$ | Sat. | None | 75-85 |

[1]Basis total olefin charge
[2]Sat. = saturated
[3]Examples V through X employ 1-butanol as a protonic promoter.

TABLE II

| | Products Weight Percent* | | | | | | Properties of Hydrogenated Stripped Oligomer | |
|---|---|---|---|---|---|---|---|---|
| Example | Monomer | Dimer | Trimer | Higher | Viscosity, cs, 210° F. | VI | Pour Point, °F. | TGA: % Sample Remaining at 233° C. |
| I | 26.0 | 59.0 | 15.0 | — | 3.75 | 123.2 | <-50 | 88.0 |
| II | 39.6 | 49.5 | 11.0 | — | 3.89 | 122.3 | <-50 | 90.4 |
| III | 100.0 | — | — | — | — | — | — | — |
| IV | 16.4 | 69.1 | 14.5 | — | 3.93 | 92.3 | <-50 | 74-78 |
| V | 4 | 37 | 41 | 18 | — | — | — | — |
| VI | 7 | 59 | 26 | 8 | 4.27 | 132 | -35 | 92.2 |
| VII | 11 | 65 | 20 | 4 | 3.92 | 125.9 | <-50 | 90.7 |
| VIII | 75 | 18 | 7 | — | — | — | — | — |
| IX | 7 | 56 | 25 | 12 | 4.16 | 135.9 | -50 | 87.3 |
| X | 20 | 56 | 16 | 8 | 3.91 | 131.4 | -50 | 90.7 |

*Before monomer removal and hydrogenation step

By comparing the examples of this invention (I and II) with the other, comparative examples of Table II, the advantage of the method of this invention become apparent. First, it may be seen that for a resin catalyst to oligomerize olefins at temperatures around 75° to 85° C., that a co-catalyst is necessary since Example III shows that NAFION by itself at 85° C. will not catalyze the reaction. Further, comparison of the oligomers produced in Examples I and II with those of IV reveals lower 210° F. viscosities, higher viscosity indices, lower pour points and better volatilities for the oligomers of the inventive method. The oligomers from Examples I and II were better in every respect than those of Example IV, including the aspect that less energy is required in Examples I and II.

When comparing the oligomers from Examples I and II with those from Examples V through X, it may be seen that the viscosity indices are somewhat lower while the volatilities are comparable for the oligomers of the inventive method. However, both the 210° F. viscosities and, to some extent, the pour points for the co-catalyst oligomers are better (lower) than for the oligomers of Examples V through X. It should also be noted that no promoter is required for the inventive method and that the solid resin co-catalyst may be quickly separated from the mixture, advantages not found when $BF_3$ only is employed. It is also somewhat easier to recycle the $BF_3$ itself when the resin is employed as opposed to the situation when only $BF_3$ and 1-butanol are present.

The method of this invention is particularly suited to the production of a "4 centistoke" fluid, such as seen as the end result of Examples I and II. Preferably, these fluids have 2 or more or less than 10 oligomer (olefin moiety) units. Their physical properties preferably include a 210° F. viscosity between 3.5 and 5.0 centistokes, a 25° C. viscosity between 25.0 and 40.0 centistokes, a viscosity index of greater than 100 and a thermogravimetric analysis value of greater than 80 weight percent remaining at 233° C.

MORE COMPARATIVE EXAMPLES

A few more comparative examples were run to show that when the feedstocks used in U.S. Pat. No. 4,300,006 are used, distillation beyond simple monomer removal is required to make a satisfactory synthetic lubricant additive.

EXAMPLE XI

Oligomerization

The oligomerization of a 70 wt.% $C_{14}$ internal olefin and 30 wt.% $C_8$ alpha olefin mixture was accomplished over 2.5 g of a boron trifluoride catalyst with 1.1 g of 1-butanol as a protonic promoter and initiated at 95.1° C.

To a dry and clean 300 ml Hastelloy C autoclave were added 119 g of $C_{14}$ internal olefin from Shell Chemical Company's Higher Olefin Process (SHOP). The double bond in these internal olefins is randomly distributed throughout the molecule. Added at the same time were 51 g of $C_8$ alpha (1-octene from Aldrich Chemical Company, Inc.). At the time this was the closest approximation possible of the U.S. Pat. No. 4,300,006 feedstock. These additions were followed by 1.1 g of 1-butanol promoter. The clave was sealed and the contents heated to 95.1° C. with stirring. Starting at 95.1° C., $BF_3$ gas was introduced by adding four shots of $BF_3$ over an 11 minute period (2.5 g total $BF_3$ added) to the stirred reaction mixture. At the end of 17 minutes (measured from the first $BF_3$ addition), the temperature had risen 110.2° C. for a maximum exotherm of 15.1° C. One hour after the first $BF_3$ addition the reaction temperature was 101.5° C. The heat was turned off and cooling water turned on. The reaction mixture was neutralized with an aqueous $Na_2CO_3$ solution and water washed twice more. The organic layer was separated and dried by filtering through folded filter paper to obtain a net weight of 156.3 g. Liquid chromatography analysis indicated 31.9% of the material was $C_8$, $C_{14}$ or $C_{16}$ and 27.5% was dimer $C_{22}$ (from $C_8$ and $C_{14}$) and 32.2% was dimer $C_{28}$ (from $C_{14}$ and $C_{14}$) while 8.3% was $C_{36}$ or heavier. Conversion to material higher than $C_6$ was about 68.1%. The ratio of dimer to trimer and heavies was 7.19:1.

Hydrogenation and Stripping

A 1-liter stirred 316 stainless steel clave was charged with 144.5 g of oligomer from the previous step and 7.2 g of a nickel-copper-chromium oxide hydrogenation catalyst. The clave was flushed with hydrogen three or four times and pressured to 1,000 psig with hydrogen. Subsequently the clave was heated to 210° C. (the pressure increased to only 1,200 psig) and pressurized again to 2,000 psig with hydrogen. The reaction mixture was stirred at 210° C. for four hours during which the pressure remained at 2,000 psig. The hydrogenated oligomer was filtered and 137.3 g subjected to high vacuum stripping. The material was distilled through a jacketed column (with about 12 inches of Goodloe packing) until the head temperature reached 105° C. at 0.06 mm Hg. The bottoms weighed 67.1 g (49.6% of the total material, overhead plus bottoms) and the overhead weighed 68.1 g (50.4% of the total material). The bottoms product has a 210° F. viscosity of 3.6 cs, a 25° C. viscosity of 27.4 cs, a pour point of < −50° F. and a viscosity index of 110. Liquid chromatography analysis indicated the presence of 25.5% dimer ($C_{22}$), 60.2% dimer ($C_{28}$) and 14.3% heavier materials. The TGA of the bottoms product indicated volatility was moderately high (85.0% sample remained at 233° C. in TGA of 10° C./minute).

EXAMPLE XII

Oligomerization

Oligomerization of a 70% $C_{14}$ internal olefin-30% $C_8$ alpha olefin mixture catalyzed by 2.2 g of $BF_3$ with 1.1 g of 1-butanol as a promoter was initiated at 94.9° C. As in the previous example, 119 g of $C_{14}$ internal olefin were added to a 300 ml clave along with 51 g of $C_8$ alpha olefin followed by 1.1 g of 1-butanol. The clave was sealed and heated to 94.9° C. Starting at 94.9° C., $BF_3$ gas was added over an 11 minute period (totalling 2.2 g of $BF_3$) to produce a 15.1° C. maximum exotherm after 16 minutes had elapsed after the first $BF_3$ addition. After a one hour reaction time measured from the first $BF_3$ addition, the mixture was cooled and neutralized with aqueous sodium carbonate. The organic layer was separated and dried by filtering through folded filter paper, to give a net weight of 162.5 g. Liquid chromatography analysis indicated 31.1% of the material was $C_8$, $C_{14}$ or $C_{16}$ and 27.2% was dimer $C_{22}$ and 33.4% was dimer $C_{28}$ while 8.3% was $C_{36}$ or heavier. Conversion to materials higher than $C_{16}$ was 68.9%. The ratio of dimer to trimer and heavies was 7.30:1.

Hydrogenation and Stripping

From the above step, 145.0 g of the oligomer was hydrogenated over 7.2 g of nickel-copper-chromium oxide catalyst. The hydrogenation was conducted at 210° C. and 2,000 psig from hydrogen for four hours. It was followed by filtration and stripping as described in the previous example. The bottoms products amounting to 55.3% of the change had a 25° C. viscosity of 25.7 cs and a 210° F. viscosity of 3.45 cs. The pour point of the bottoms material was −40° F. and the viscosity index was 109.0. Liquid chromatography analysis indicated 33.6% dimer $C_{22}$ and 53.8% dimer $C_{28}$ and 12.6% heavies. The ratio of dimer to trimer and heavier was thus 6.94:1. The TGA indicated that the material was definitely too volatile; 82.1% sample remaining.

EXAMPLE XIII

Oligomerization

Oligomerization of a 70% $C_{14}$ internal olefin-30% $C_8$ alpha olefin mixture catalyzed by 2.5 g $BF_3$ and 1.1 g 1-butanol as promoter was conducted starting at 75.1° C. To a clean and dry 300 ml clave were added 119 g of $C_{14}$ internal olefin and 51 g of $C_8$ alpha olefin of the same sources as the previous two examples, followed by 1.1 g of 1-butanol promoter. The clave was sealed and heated to 75.1° C. and at that temperature $BF_3$ gas was added in increments (shots) over a 10 minute period. Five separate shots were applied to total 2.5 g. Eleven minutes after the first $BF_3$ addition, the reaction temperature had risen to 100.7° C. (a maximum exotherm of 25.6° C.). The reaction was held at 75° C. for 1.5 hours total and then cooled and worked up as in the previous examples. The dry product from this lower temperature oligomerization had the following liquid chromatography analysis: 12.7% of monomer ($C_8$, $C_{14}$ and $C_{16}$), 23.7% of $C_{22}$, 42.1% of $C_{28}$ and 21.4% of trimer and heavies. Conversion to materials greater than $C_{16}$ was 87.3% with the dimer to trimer and heavies being 3.07:1.

Hydrogenation and Stripping

Hydrogenation of the oligomer from the above step was completed at 210° C., 4.0 hours and 2,000 psig hydrogen pressure. Workup (filtration) followed by high vacuum stripping afforded a bottoms product which amounted to 70.7% of the charge and had the following properties: 210° F. viscosity of 4.16 cs, 25° C. viscosity of 34.5 cs, pour point of <50° F. and a viscosity index of 124.2. The liquid chromatography analysis indicated 16.7% of the material was $C_{22}$, 56.8% was $C_{28}$ and 26.5% was heavies. TGA indicated the sample had excellent volatility (90% remaining at 233° C.).

EXAMPLES XIV–XXII

Examples XIV–XIX were conducted in a manner similar to Examples XI–XIII except that certain parameters were changed as shown in Table III.

Examples XX–XXII were conducted according to the following procedure. Eighty-three grams of delta 7 $C_{14}$ and 36 g of delta 9 $C_{18}$ internal olefin and 51 g of $C_8$ alpha olefin were added to a 300 ml Hastelloy clave followed by 1.1 g of 1-butanol. This olefin mixture is the closest approximation to the U.S. Pat. No. 4,300,006 feedstocks obtainable with the materials on hand. The clave was sealed and $BF_3$ introduced in the indicated quantities. Workup was conducted as usual involving an aqueous $Na_2CO_3$ wash followed by two water washes and filtering the organic layer through filter paper to dry it. Hydrogenation was accomplished at 210° C. and in the presence of 5% (by weight, basis olefin) nickel catalyst and 2,000 psig hydrogen pressure for four hours. The hydrogenation product was filtered and distilled at high vacuum (<0.1 mm Hg) and to a head temperature of 110° C. The bottoms product was submitted for analysis. The results of this last set of comparative examples are summarized in Table III.

TABLE III

EXPERIMENTS USING LOWER MOLECULAR WEIGHT ALPHA AND HIGHER MOLECULAR WEIGHT INTERNAL OLEFINS AS FEEDSTOCKS

| Ex. | Feedstock, wt. %, Internal | Alpha | Reaction Temp., °C. | Reaction Time, Hours | $BF_3$ Added, Grams | Maximum Exotherm, °C. | Liquid Chromatography Conv. | Dimer, Trimer and Heavies | % Bottoms | Centistokes, 210° F. | 25° C. | VI | Pour Point, °F. | TGA |
|---|---|---|---|---|---|---|---|---|---|---|---|---|---|---|
| XI | 70 $C_{14}$ | 30 $C_8$ | 95.1–110.2 | 1.0 | 2.5 | 15.1 | 68.1 | 7.19:1 | 49.6 | 3.80 | 27.4 | 110.0 | <−50 | 85.0 |
| XII | 70 $C_{14}$ | 30 $C_8$ | 94.9–110.0 | 1.0 | 2.2 | 15.1 | 68.9 | 7.30:1 | 55.3 | 3.45 | 25.7 | 109.0 | −40 | 82.1 |
| XIII | 70 $C_{14}$ | 30 $C_8$ | 75.1–100.7 | 1.5 | 2.5 | 25.6 | 87.3 | 3.07:1 | 70.7 | 4.16 | 34.5 | 124.2 | <−50 | 90.0 |
| XIV | 70 $C_{14}$ | 30 $C_8$ | 75.0–96.4 | 1.5 | 2.5 | 21.9 | 93.5 | 1.55:1 | — | — | — | — | — | 86.0 |
| XV | 48.8 Δ7 $C_{14}$ + 21.2 Δ9 $C_{18}$ | 30 $C_8$ | 75.1–97.4 | 1.5 | 2.1 | 22.3 | 83.1 | — | 83.5 | 3.41 | 24.3 | 108.9 | +20 | 76.4 |
| XVI | 70 $C_{14}$ | 30 $C_8$ | 25.0–47.8 | 1.5 | 2.6 | 22.8 | 82.0 | 3.74:1 | 81.9 | 4.91 | 40.8 | 138.6 | −15 | 92.9 |
| XVII | 70 $C_{14}$ | 30 $C_8$ | 25.0–28.1 | 6.5 | 2.4 | 3.1* | 21.4 | 6.38:1 | 15.5 | — | — | — | — | 83.8 |
| XVIII | 70 $C_{14}$ | 30 $C_8$ | 25.0–54.5 | 1.5 | 5.4 | 29.4 | 96.9 | 0.93:1 | 93.5 | 4.99 | 45.0 | 125.6 | −35 | 92.0 |
| XIX | 70 $C_{14}$ | 30 $C_8$ | 25.0–55.8 | 6.5 | 5.4 | 30.7 | 97.3 | 0.65:1 | 92.8 | 5.91 | 58.4 | 126.9 | −45 | 93.6 |
| XX | 48.8 Δ7 $C_{14}$ + 21.1 Δ9 $C_{18}$ | 30 $C_8$ | 25.2–44.4 | 1.5 | 2.5 | 19.2 | 86.1 | — | 72.0 | 4.40 | 37.1 | 120.3 | <−50 | 90.3 |
| XXI | 48.8 Δ7 $C_{14}$ + 21.1 Δ9 $C_{18}$ | 30 $C_8$ | 25.1–41.7 | 1.5 | 5.1 | 21.6 | 93.1 | — | 85.0 | 4.67 | 39.2 | 123.6 | <−50 | 90.0 |
| XXII | 48.8 Δ7 $C_{14}$ + 21.1 Δ9 $C_{18}$ | 30 $C_8$ | 25.1–51.1 | 6.5 | 5.5 | 26.0 | 96.4 | — | 85.2 | 5.63 | 54.0 | 123.2 | −40 | 94.0 |

*This reaction never started.

As can be seen from Table III, the product from the feedstocks used in U.S. Pat. No. 4,300,006 are unsuitable for use as a synthetic lubricant without further distillation; i.e., the bottoms product found useful using the method of the invention are superior. Examples XX–XXII have 210° F. and 25° C. viscosities which are too high for use as 4 cs synthetic lubricants. One skilled in the art would not expect these materials to pass cold cranking tests. These same feedstocks when run at a higher temperatures produce a material with a low viscosity index and a poor TGA value (see Example XV).

Thus it is determined by comparative examples using the conditions of U.S. Pat. No. 4,300,006 that the resulting products would need to be distilled in order to meet the 4.0 cs 210° F. viscosity requirement and apparently the cold-cranking specifications as well. Examples XVI–XIX utilizing the feeds of this invention with the U.S. Pat. No. 4,300,006 conditions indicate similar and in some cases worse results; the products had higher 210° F. viscosities and higher pour points than desired.

Many modifications in the method of this invention may be made by one skilled in the art without departing from the spirit and scope of this invention which are defined only by the appended claims. For example, the olefin feed, the reaction temperature, the pressure and the modes of addition could be optimized for better yields.

We claim:

1. A method for the production of olefin oligomers comprising reacting a mixture of alpha olefins and internal olefins in the presence of boron trifluoride and a cationic ion exchange resin under oligomerization conditions, the mixture of olefins being comprised of greater than 50 weight percent internal olefins.

2. The method of claim 1 in which both the alpha and internal olefins each have between 9 and 24 carbon atoms, inclusive.

3. The method of claim 1 in which both the alpha and internal olefins each have between 13 and 15 carbon atoms, inclusive.

4. The method of claim 1 in which the alpha and internal olefin mixture contains alpha and internal olefins that have carbon numbers identical to or within one carbon of each other and in which the internal olefins have the double bond randomly distributed.

5. The method of claim 1 in which the ion exchange resin is a perfluorosulfonic acid resin.

6. The method of claim 1 in which the oligomerization reaction is conducted at a temperature in the range of 25° to 100° C. and at a pressure in the range of ten to 2,000 psig.

7. The method of claim 1 in which the oligomerization reaction is conducted at a temperature in the range of about 75° to 85° C.

8. The method of claim 1 in which the amount of ion exchange resin is between about 0.1 and 10 weight percent of the total olefin charge.

9. The method of claim 1 in which the amount of ion exchange resin is about 2 weight percent of the total olefin mixture.

10. The method of claim 1 in which the oligomerized olefins are hydrogenated.

11. The method of claim 10 in which the hydrogenation takes place over a catalyst selected from the group of catalysts consisting of nickel-copper-chromia and cobalt-copper-chromia.

12. A synthetic lubricant component prepared according to the method of claim 1.

13. A method for the production of olefin oligomers comprising
(a) reacting a mixture of alpha olefins and internal olefins, both the alpha and internal olefins having between 9 and 24 carbon atoms, inclusive, in the presence of boron trifluoride and a cationic ion exchange resin in an amount of 0.1 to 10 weight percent of the total olefin mixture at a temperature in the range of 25° to 100° C., the mixture of olefins being comprised of greater than 50 weight percent internal olefins,
(b) hydrogenating the resulting oligomers in the presence of hydrogen and a hydrogenation catalyst, and
(c) separating out any unreacted monomer as the only separation step.

14. The method of claim 13 in which both the alpha and internal olefins each have between 13 and 15 carbon atoms, inclusive.

15. The method of claim 13 in which the alpha and internal olefin mixture contains alpha and internal olefins that have carbon numbers identical to or within one carbon of each other and in which the internal olefins have the double bond randomly distributed.

16. The method of claim 13 in which the ion exchange resin is a perfluorosulfonic acid resin.

17. The method of claim 13 in which the oligomerization reaction is conducted at a temperature in the range of about 75° to 85° C.

18. The method of claim 13 in which the amount of ion exchange resin is about 2 weight percent of the total olefin mixture.

19. The method of claim 13 in which the hydrogenation takes place over a catalyst selected from the group of catalysts consisting of nickel-copper-chromia and cobalt-copper-hromia.

20. A synthetic lubricant component prepared according to the method of claim 13.

21. A method for the production of olefin oligomers comprising
(a) reacting a mixture of alpha olefins and internal olefins, both the alpha and internal olefins having between 9 and 24 carbon atoms, inclusive, in the presence of boron trifluoride and a perfluorosulfonic acid cationic ion exchange resin in an amount of about 2 weight percent of the total olefin mixture at a temperature in the range of 75° to 85° C., the mixture of olefins being comprised of greater than 50 weight percent internal olefins,
(b) hydrogenating the resulting oligomers in the presence of hydrogen and a hydrogenation catalyst, and
(c) separating out any unreacted monomer as the only separation step.

22. The method of claim 21 in which both the alpha and internal olefins each have between 13 and 15 carbon atoms, inclusive.

23. The method of claim 21 in which the alpha and internal olefin mixture contains alpha and internal olefins that have carbon numbers identical to or within one carbon of each other and in which the internal olefins have the double bond randomly distributed.

24. The method of claim 21 in which the hydrogenation takes place over a catalyst selected from the group of catalysts consisting of nickel-copper-chromia and cobalt-copper-chromia.

25. A synthetic lubricant component prepared according to the method of claim 21.

26. A method for the production of olefin oligomers comprising
(a) mixing alpha olefins with internal olefins such that the internal olefins comprise greater than 50 weight percent of the mixture, and such that both the alpha and internal olefins have between 13 and 15 carbon atoms, inclusive, and such that the internal olefins have the double bond randomly distributed,
(b) reacting the components of the mixture in the presence of boron trifluoride and a perfluorosulfonic acid cationic ion exchange resin in an amount of 0.1 to 10 weight percent of the total olefin mixture at a temperature in the range of 75° to 85° C.,
(c) hydrogenating the resulting oligomers in the presence of hydrogen and a hydrogenation catalyst, and
(d) separating out any unreacted monomer as the only separation step.

27. The method of claim 26 in which the amount of ion exchange resin is about 2 weight percent of the total olefin mixture.

28. The method of claim 26 in which the hydrogenation takes places over a catalyst selected from the group of catalysts consisting of nickel-copper-chromia and cobalt-copper-chromia.

29. A synthetic lubricant component prepared according to the method of claim 26.

30. A method for the production of olefin oligomers suitable for use as synthetic lubricant base oils comprising contacting a mixture of alpha and internal mono olefins where internal olefins comprise greater than 50 weight percent of the mixture with a boron trifluoride catalyst and a cationic ion exchange resin under oligomerization conditions, to form oligomers composed of 2 or more but less than 10 oligomer units.

31. The method of claim 30 in which both the alpha and internal olefins each have between 9 and 24 carbon atoms.

32. A method for the production of olefin oligomers suitable for use as synthetic lubricant base oils comprising contacting a mixed mono olefin feedstock comprising (a) a first olefin component comprising one or more alpha olefins having the formula

R"CH=CH$_2$ where R" is an alkyl radical of 7 to 22 carbon atoms, and (b) greater than 50 weight percent of a second olefin component comprising one or more internal olefins having the formula

RCH=CHR' where R and R' are the same or different alkyl radicals of 1 to 21 carbon atoms, except that the total number of carbon atoms is between 9 and 24, inclusive, with a boron trifluoride catalyst and a cationic ion exchange resin under oligomerization conditions to form synthetic lubricant components having a viscosity at 210° F. of between 3.5 and 5.0 centistokes, a viscosity at 25° C. of between 25.0 and 40.0 centistokes, a viscosity index of greater than 100 and a thermogravimetric analysis value of greater than 80 weight percent.

33. The method of claim 30 or 32 in which both the alpha and internal olefins each have between 13 and 15 carbon atoms, inclusive.

34. The method of claim 30 or 32 in which the alpha and internal olefin mixture contains alpha and internal olefins that have carbon numbers identical to or within one carbon of each other and in which the internal olefins have the double bond randomly distributed.

35. The method of claim 30 or 32 in which the ion exchange resin is a perfluorosulfonic acid resin.

36. The method of claim 30 or 32 in which the oligomerization reaction is conducted at a temperature of the range of 25° to 100° C. and at a pressure in the range of 10 to 2,000 psig.

37. The method of claim 30 or 32 in which the oligomerization reaction is conducted at a temperature in the range of about 75° to 85° C.

38. The method of claim 30 or 32 in which the amount of ion exchange resin is between about 0.1 and 10 weight percent of the total olefin charge.

39. The method of claim 30 or 32 in which the amount of ion exchange resin is about 2 weight percent of the total olefin mixture.

40. The method of claim 30 or 32 in which the oligomerized olefins are hydrogenated.

41. The method of claim 30 or 32 in which the oligomerized olefins are hydrogenated over a catalyst selected from the group of catalysts consisting of nickel-copper-chromia and cobalt-copper-chromia.

42. A synthetic lubricant component prepared according to the method of claim 30 or 32.

* * * * *